(12) United States Patent
Berwick et al.

(10) Patent No.: US 8,964,937 B2
(45) Date of Patent: Feb. 24, 2015

(54) METHODS AND SYSTEMS IN RADIOTHERAPY

(71) Applicant: Elekta AB (publ), Stockholm (SE)

(72) Inventors: Paul Berwick, Crawley (GB); Christopher Knox, East Grinstead (GB)

(73) Assignee: Elekta AB (publ), Stockholm (SE)

( * ) Notice: Subject to any disclaimer, the term of this patent is extended or adjusted under 35 U.S.C. 154(b) by 113 days.

(21) Appl. No.: 13/896,412

(22) Filed: May 17, 2013

(65) Prior Publication Data

US 2014/0341351 A1   Nov. 20, 2014

(51) Int. Cl.
*A61N 5/10* (2006.01)
*A61B 6/10* (2006.01)

(52) U.S. Cl.
CPC .................................. *A61N 5/1045* (2013.01)
USPC ............................. 378/65; 378/207; 378/210

(58) Field of Classification Search
CPC ............. A61B 6/00; A61B 6/04; A61B 6/08; A61B 6/10; A61B 6/40; A61B 6/42; A61B 6/52; A61B 6/58; A61B 6/586; A61B 6/54; A61N 5/00; A61N 5/10; A61N 5/103; A61N 5/1048; A61N 5/1075

USPC .......... 378/62, 65, 91, 95, 162, 204, 207, 210
See application file for complete search history.

(56) References Cited

U.S. PATENT DOCUMENTS

| | | | | |
|---|---|---|---|---|
| 3,891,856 | A | * | 6/1975 | Amor et al. .................... 378/197 |
| 4,868,844 | A | | 9/1989 | Nunan ........................... 378/152 |
| 5,012,506 | A | | 4/1991 | Driver et al. .................. 378/152 |
| 2008/0080671 | A1 | * | 4/2008 | Nakayama ...................... 378/97 |
| 2008/0187097 | A1 | * | 8/2008 | Cheng et al. .................... 378/65 |
| 2011/0121763 | A1 | | 5/2011 | Sadler ............................ 315/505 |
| 2012/0228521 | A1 | * | 9/2012 | Honda et al. ............... 250/492.3 |
| 2013/0142309 | A1 | * | 6/2013 | Iwakiri et al. ................... 378/62 |

* cited by examiner

*Primary Examiner* — Anastasia Midkiff
(74) *Attorney, Agent, or Firm* — Sunstein Kann Murphy & Timbers LLP

(57) ABSTRACT

A method of operating a radiotherapy system, comprising: receiving a treatment plan to be carried out using the radiotherapy system; detecting if there is a fault in a component of the radiotherapy system; determining whether the component is needed for delivery of the treatment plan; and if the component is not needed for delivery of the treatment plan, allowing the radiotherapy system to execute the treatment plan.

14 Claims, 3 Drawing Sheets

METHODS AND SYSTEMS IN RADIOTHERAPY

TECHNICAL FIELD

The present invention relates to radiotherapy, and particularly to methods and systems for operating radiotherapy systems.

BACKGROUND

Radiotherapy involves the application of ionizing radiation to a target within a patient (e.g. a tumour) so as to damage the unhealthy cells within the target, eventually causing cell death through one or multiple exposures. The radiation is harmful to both the unhealthy tissue within the target and the healthy tissue which surrounds it, and thus much research has been focussed on maximizing the radiation dose within the target while minimizing the dose outside the target.

Prior to beginning a course of radiotherapy, volumetric images of the patient, and specifically the target region, need to be obtained so that a plan for the treatment can be constructed. The aim of the treatment plan is to establish how to apply the radiotherapy to the patient so that the target region receives the desired dose, whilst the surrounding healthy tissue receives as little dose as possible.

Radiation is delivered in one or more beams of high-energy radiation directed towards a patient. The patient typically lies on a couch or patient support, and the beam is directed toward the patient from an offset location. During treatment, the beam source is rotated around the patient while keeping the beam directed toward the target point. The result is that the target remains in the beam at all times, but areas immediately around the target are irradiated only briefly by the beam during part of its rotation. In this way, the dose to the tumour is maximised whilst the dose to surrounding healthy tissue is reduced.

The cross-section of the beam can be varied by way of a range of types of collimator, such as the so-called "multi-leaf collimator" (MLC) illustrated in EP 0,314,314. The MLC comprises one or more banks of thin, elongate leaves, each movable across the radiation beam to a greater or lesser extent in order to block the radiation. Collectively, the bank of leaves defines a shaped profile which is imparted to the radiation beam. These can be adjusted during treatment so as to create a beam whose cross-section varies dynamically as it rotates around the patient.

Other aspects of the radiotherapy apparatus can also be varied during treatment, such as the speed of rotation of the source and the dose rate. The patient table supporting the patient during therapy may allow movement of the patient during therapy, so as to place the target at an optimum position for treatment. There are a large number of variables offered by the apparatus in order to tailor the radiation dose that is delivered to the patient.

The volumetric images are therefore analysed to identify a target region into which a minimum dose is to be delivered, any sensitive regions such as functional organs for which a maximum dose must be observed, and other non-target regions into which the dose is to be generally minimised. This three-dimensional map must then be used to develop a treatment plan, i.e. a sequence of source movements, collimator movements, and dose rates which result in a three-dimensional dose distribution that (a) meets the requirements as to maximum and minimum doses (etc) and (b) is physically possible, e.g. does not require the source to rotate around the patient faster than it is physically capable.

The treatment plan is therefore a set of instructions to be carried out by the various components of the radiotherapy system in order to have a particular therapeutic effect in the patient.

Throughout the treatment process, safety of the patient is paramount. To this end, prior to treatment, each treatment plan is carefully reviewed, with complex plans being tested first on a phantom to check the radiation dose distribution is as expected. If an unexpected or otherwise unacceptable radiation dose results from the treatment plan, a revised treatment plan can be generated.

Further, each component of the radiotherapy system is monitored prior to and during treatment to ensure it is working correctly. If a component develops a fault, the treatment can be suspended immediately to reduce the potential for harm to the patient.

The nature of such monitoring depends on the particular component. However, as an example, it is known to place a marker at the tip of each MLC leaf and to monitor the leaf positions using a camera. By comparing the actual leaf positions with the expected leaf positions, the functioning of the MLC leaves can be tracked.

SUMMARY OF INVENTION

When one of the components in a radiotherapy system develops a fault of any nature, that radiotherapy system is automatically deemed completely inoperable. The system cannot be used until the faulty component is repaired or replaced. While this certainly ensures the safety of the patients and operating staff, it is somewhat inefficient as the system can be placed out of operation for hours, days or even weeks depending on the nature of the fault. In this time, patients who would have been treated on the machine may have to travel to a different care centre, or have their treatment delayed if acceptable.

It will be apparent from the description above that radiotherapy systems have a large number of separate components, and are capable of implementing a wide range of treatment plans. However, not all of those components will be needed to deliver any particular treatment plan.

According to a first aspect of the present invention, there is provided a method of operating a radiotherapy system, comprising: receiving a treatment plan to be carried out using the radiotherapy system; detecting a fault in a component of the radiotherapy system; determining whether the component is needed for delivery of the treatment plan; and if the component is not needed for delivery of the treatment plan, allowing the radiotherapy system to execute the treatment plan.

Thus the present invention provides a method whereby radiotherapy systems are no longer deemed either "operable" or "inoperable". The present invention provides that radiotherapy systems may be deemed "operable for certain treatment plans", provided that those treatment plans can be delivered safely and accurately using the fully functional components of the system. In this way the patients and operating staff are not inconvenienced, and the radiotherapy system can be kept in use for longer periods of time until the faulty component can be replaced, thus helping to maintain a steady throughput of patients in the facility.

The invention may also be embodied by a computer program product, comprising code which, when executed by one or more processors, cause those processors to carry out the methods described above and below.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

The present invention relates to a method and a computer program product for controlling radiotherapy systems. Radiotherapy systems can take a number of different forms, having different components and employing different treatment methodologies. Embodiments of the present invention are applicable to each of these systems. Two examples of such radiotherapy systems are shown and described with respect to FIGS. 1 and 2.

Figure 1:
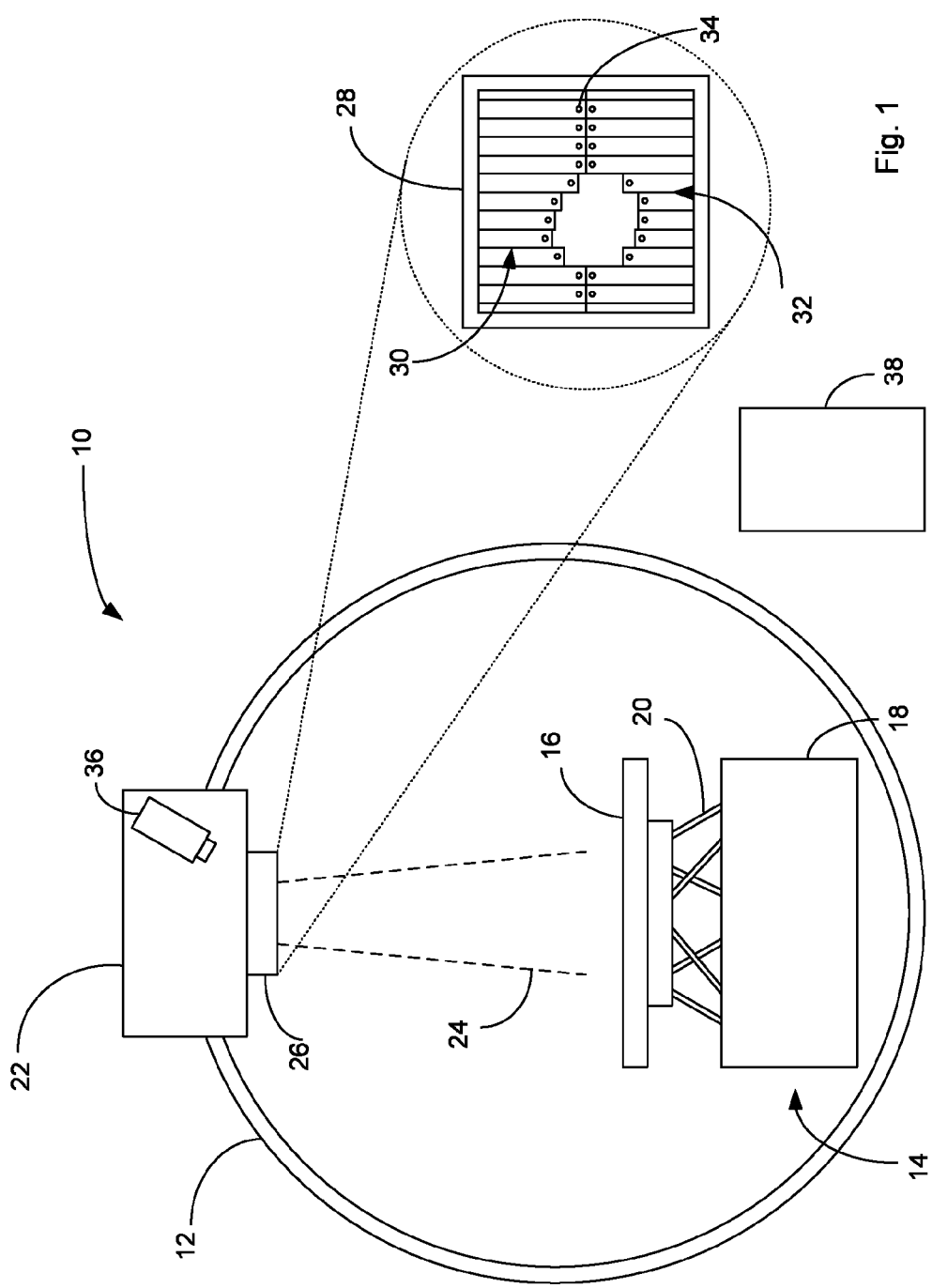
FIG. 1 shows a radiotherapy system according to embodiments of the present invention.

FIG. 1 shows a radiotherapy system 10 according to embodiments of the present invention. The system comprises a gantry 12 which is able to rotate about an axis I (extending into and out of the page in the Figures). In the illustrated embodiment the gantry 12 is depicted as a circular ring for simplicity, but those skilled in the art will appreciate that the gantry 12 may take any convenient form. For example, one or more C-arms may be used as the gantry, supporting components and being able to rotate about an axis.

A patient support 14 is located on or near the rotation axis I, and in operation serves to support a patient undergoing therapy. The patient support comprises a bed 16, on which the patient can sit or recline during treatment, and a number of support mechanisms with which the position and/or orientation of the bed 16 can be adjusted. One or more first support mechanisms 18 may allow relatively coarse adjustments of the bed position and/or orientation in one or more degrees of freedom. For example, the first support mechanisms may be used for one or more of the following: translation of the bed 16 in three degrees of freedom (i.e. height adjustment, two-dimensional positioning within the system 10), and rotation of the bed 16 in one degree of freedom (e.g. rotation about an axis substantially perpendicular to the floor). One or more second support mechanisms 20 may allow relatively fine adjustment of the bed position and/or orientation in one or more degrees of freedom. In the illustrated embodiment, the second support mechanisms 20 comprise a hexapod. The hexapod comprises six members arranged at oblique angles to each other between the bed 16 and the first support mechanisms 18. Each member can be individually extended or retracted such that, by collectively adjusting the respective extending members, the orientation and position of the bed 16 can be adjusted in up to six degrees of freedom (i.e. x, y, z, pitch, yaw and roll). In the illustrated embodiment, compared to the first support mechanisms 18, the second support mechanisms 20 allow relatively fine adjustment of the bed position and/or orientation.

Although in the illustrated embodiment the second support mechanisms 20 are illustrated between the first support mechanisms 18 and the bed 16, it will be apparent to those skilled in the art that any arrangement of support mechanisms for adjusting the orientation and/or position of the bed 16 may be employed without departing from the scope of the present invention. For example, the first support mechanisms 18 could be coupled between the second support mechanisms 20 and the bed 16.

A source of therapeutic radiation 22 is mounted on the gantry 12 and directed inwards towards the axis of rotation I. In some embodiments of the present invention, the source 22 comprises a linear accelerator, or linac, arranged to accelerate charged particles (such as electrons) to relativistic speeds and energies in the megavoltage (MV) range. In one embodiment, the charged particles are used to treat the patient directly, typically for targets on or near the surface of the patient. In other embodiments, the particles are fired towards a high-density target (e.g. tungsten) to generate secondary radiation via mechanisms such as Bremsstrahlung radiation. The secondary radiation so generated includes x-rays up to and including the energy of the charged particle, which are then used to treat the patient.

In other embodiments, the source of therapeutic radiation 22 may comprise one or more radioactive sources, such as cobalt-60, or any other means of generating energetic, ionizing radiation.

The therapeutic radiation generated by the source 22 is collimated into a beam 24 having a primary shape (cone-shaped and fan-shaped beams are well known but other shapes are possible) defined by one or more primary collimators. Further collimation is performed by secondary collimators 26, to adapt the beam to take a desired cross section. Typically the primary collimators will be fixed in place such that the overall shape of the treatment beam (i.e. before secondary collimation) is not changed during treatment. The secondary collimators tend to be more complex, however, and these may be updated during treatment to ensure the treatment beam conforms to a desired cross section.

In the illustrated embodiment the secondary collimator is a multi-leaf collimator (MLC). A beam's eye view of the MLC 26 is illustrated in the detail circle of FIG. 1. The MLC comprises a housing 28 defining a radiation window through which the radiation beam passes. One or more banks of parallel leaves 30, 32 are arranged to the side of the radiation window, with a common arrangement being to have two banks of parallel leaves arranged on opposing sides of the window as illustrated. Each bank of leaves comprises a plurality of leaves arranged side-by-side in a lateral direction, perpendicular to the beam axis. Each leaf is relatively narrow in that lateral direction, and relatively long in a longitudinal direction (perpendicular to both the beam axis and the lateral direction). Each leaf may be manufactured from a high-density material (such as tungsten), and has a significant depth in the direction of the beam axis in order to block the radiation from passing through. In use, the leaves are individually controllable to extend in the longitudinal direction across the radiation window to a greater or lesser extent as required. In one embodiment, each leaf can be extended across the entire radiation window or withdrawn from the entire radiation window, and can be arranged to take any position in between those two extremes. The leaves can therefore be positioned so as to define an aperture through the window of an arbitrary shape, thus collimating the radiation beam to conform to that shape.

Each leaf further comprises a marker 34 positioned towards its tip. Each marker 34 provides a means for tracking the location of the leaf tip, and can for example comprise a reflective surface or a fluorescent material. A source of light (not illustrated) incident upon the markers 34 will cause them to fluoresce or reflect the light, so making the leaf tips more visible. A camera 36 is arranged within the system 10 to track the location of each marker 34 and therefore the location of each leaf. In the illustrated embodiment the camera 36 is positioned within the radiation head of the source 22. However, in other embodiments the camera 36 may be positioned anywhere that it has a clear view of the markers 34.

Thus in one embodiment the collimator 26 is a multi-leaf collimator as described above. The combined effect of the source 22 and the collimator 26 is to produce a beam of radiation 24 having a collimated shape and an energy (typically in the MV range) which has a therapeutic effect in the patient. In use, the beam 24 is directed generally towards the rotation axis I of the gantry 12. A patient is positioned on the bed 16 such that the target for treatment lies on or near the rotation axis I. Rotation of the gantry 12 during treatment causes the beam 24 to be directed towards the target from multiple directions. The target remains in the treatment beam for most (or all) of the time and thus radiation dose accumulates to a relatively high level there. The surrounding healthy tissue also lies within the radiation beam 24 but only for a limited period of time before the gantry rotates and the beam passes through a different part of the patient. Radiation dose in the healthy tissue is therefore kept at a relatively low level.

A controller 38 is coupled to one or more of the radiation source 22, the collimators 26, the camera 36 and the patient support 14, and controls the operation of each component prior to and during treatment. The controller 38 may comprise any suitable device, such as a computer. The controller 38 may have one or more programs stored thereon for controlling the system 10 according to embodiments of the present invention.

Figure 2:
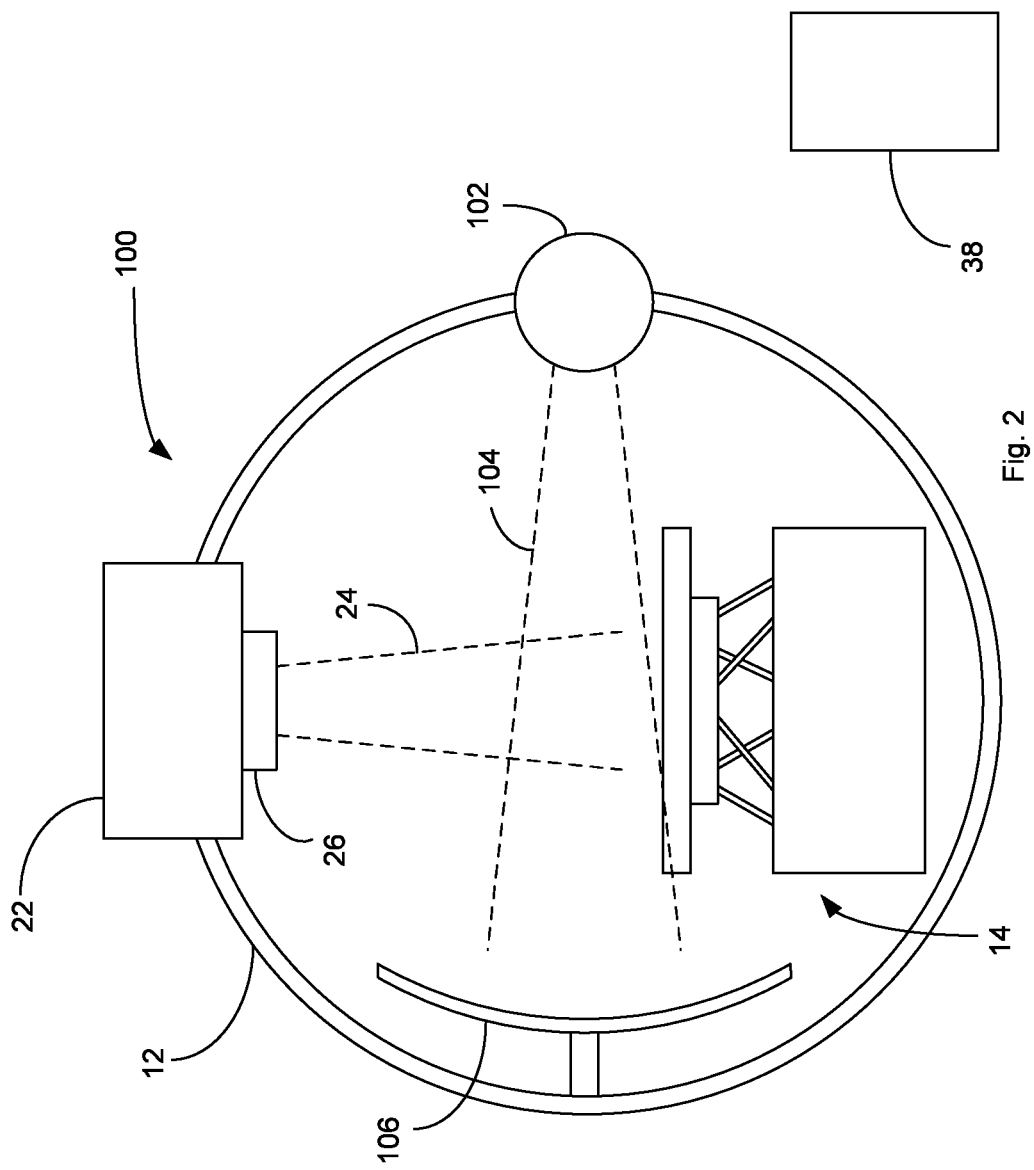
FIG. 2 shows a radiotherapy system according to further embodiments of the present invention.

FIG. 2 shows a radiotherapy system 100 according to further embodiments of the present invention. The system 100 has many components in common with the system 10 described above, and these will not be described again in any detail. Like components are given like reference numerals.

The system 100 therefore comprises a rotatable gantry 12, a patient support 14, a source of radiation 22 producing a beam of therapeutic radiation 24, one or more secondary collimators 26, and a controller 38.

The system 100 further comprises a second source of radiation 102, also mounted on the gantry 12. This source 102 generates radiation which is suitable for imaging (e.g. x-rays in the kV range), and provides a beam of radiation 104 directed inwards towards the rotation axis I of the gantry 12. In one embodiment the beam of imaging radiation 104 has a cone shape, as suitable for use in cone beam computed tomography (CBCT), but other shapes are possible. The imaging radiation may be pulsed or continuous.

A detector 106 is mounted on the gantry 12 opposite the source of imaging radiation 102, and is arranged to capture the imaging radiation 104 after it has passed through, and been attenuated by, the patient. Knowledge of the attenuated radiation (i.e. the imaging data), the source of radiation 102 and the attenuation mechanism allows the imaging data to be back-projected to generate a tomographic image of the patient. An imaging device (not illustrated) may be connected to the detector 106 and processes the data sampled there to generate images of the patient.

The source of imaging radiation 102 and the detector 106 can be operated during treatment in order to provide real-time feedback on the position of the target within the patient. This method of operation is particularly useful where the target undergoes periodic variation due to a physiological cycle. For example, a target near the lungs may move cyclically due to the respiration cycle; a target near the heart may move cyclically due to the cardiac cycle. By providing real-time imaging, the radiation can be directed and shaped more accurately to conform to the current location of the target.

Embodiments of the present invention are applicable to a wide range of radiotherapy systems, and the systems described above are given as examples to which embodiments of the present invention might apply. However, it will be apparent to the skilled person that embodiments of the present invention apply equally to radiotherapy systems employing a subset of the components described above, and to radiotherapy systems employing a combination of the components which are described above only in separate systems. For example, a radiotherapy system may comprise a source of imaging radiation and a detector, as well as a hexapod patient support. Any combination of the components described in FIGS. 1 and 2 may be employed.

Figure 3:
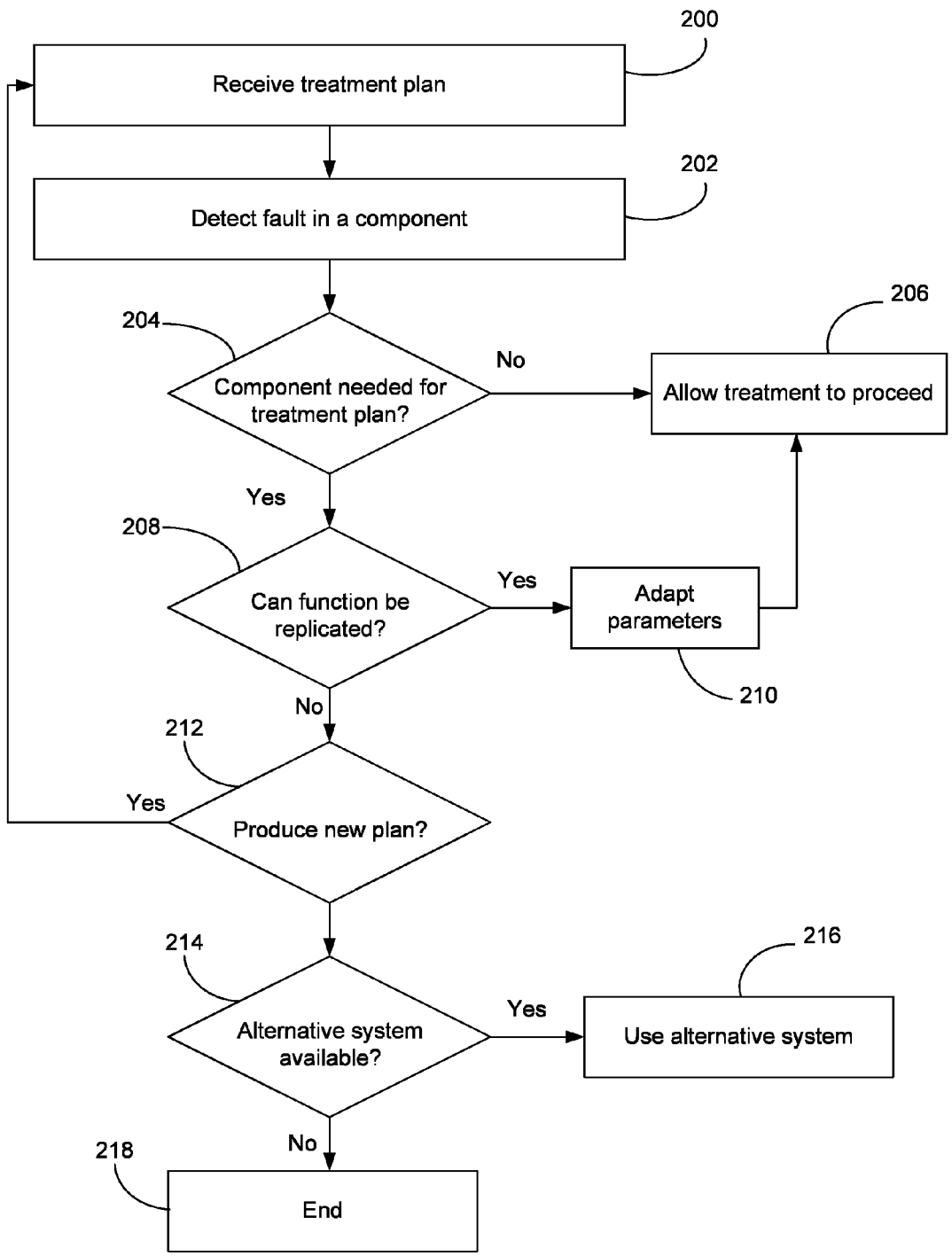
FIG. 3 is a flow chart of a method according to embodiments of the present invention.

FIG. 3 is a flow chart of a method according to embodiments of the present invention. The method may be carried out by the controller 38 described above, for example.

The method begins in step 200, where a radiotherapy treatment plan is received. The treatment plan will have been previously formulated by a treatment planning apparatus on the basis of a planning image of the patient (i.e. an image incorporating the target for treatment as well as the surrounding tissue and anatomical structures), a number of clinical objectives set by a clinician (e.g. a minimum dose for the target, a maximum dose for radiation-sensitive nearby structures, etc), and the constraints of the radiotherapy system which is to apply the therapy. The treatment plan comprises a set of instructions to be carried out by the various components of the system to have a particular therapeutic effect in the patient.

In step 202, a fault is detected in one of the components of the system. The fault may occur prior to treatment (or even prior to receipt of the treatment plan in step 200) or during treatment. Each radiotherapy system has many components and, although they are designed and manufactured to be extremely durable, reliable and accurate, faults may occur from time to time.

For example, the camera 36 records imaging data of the MLC leaf positions and feeds this back to the controller 38. It may happen that the controller 38 detects that one of the MLC leaves is not operating correctly. Through tracking the positions of the markers 34 and comparing them to expected positions, the controller 38 may find that one of the MLC leaves is stationary when it should be moving, or is at the wrong location for example. This could be because the drive mechanism for that particular leaf has developed a fault.

One or more of the support mechanisms 18, 20 in the patient support 14 may develop a fault. Feedback sensors in the support mechanisms 18, 20 may send a warning signal to the controller 38 indicating the nature of the problem. For example, one of the first and second support mechanisms may no longer be capable of moving in one or more degrees of freedom. One of the first support mechanisms may fail, or one or more of the hexapod members may fail. In either case, the ability of the patient support 14 to move in all degrees of freedom may be compromised.

In radiotherapy systems employing an imaging system, the imaging system may develop a fault. For example, one or more elements in the detector may become unable to detect and record imaging data, or the source of imaging radiation may overheat and not be able to operate to its usual level. If this happens, the imaging system may send a suitable signal to the controller 38 warning it of the situation.

Thus there are various faults which could be detected in step 202. Ordinarily, any fault would lead to the whole system being deemed inoperable. However, according to embodiments of the present invention, the method proceeds to step 204 where it is determined whether the faulty component is needed to deliver the treatment plan. For example, it can be determined whether the faulty component is to be used to delivery the treatment plan.

For example, if the fault is within the imaging system, it may be that the particular treatment plan does not require any imaging steps. In that case, once the faulty imaging system is compared to the treatment plan, it can be determined that the treatment plan is not adversely affected by the faulty imaging system. The imaging system is not needed to deliver the treatment plan.

If the fault is with one of the MLC leaves, it may be the case that the particular leaf is not moved during delivery of the treatment plan. For example, it is common for the dynamic radiation beam collimation (that is, collimation which changes during treatment) to occur at or near the centre of the radiation window defined by the housing 28. Leaves towards the outer edge of the window are moved less frequently, and it may be that some treatment plans do not require those leaves to move at all during treatment (i.e. they are set to the same, closed position throughout the treatment). Provided the leaves can be set to that position, they are not needed for delivery of the treatment plan. Or, put another way, the drive mechanism for the leaf is not needed to deliver the treatment plan.

In another alternative scenario, the patient support 14 may be unable to move in a particular degree of freedom (i.e. rotation or translation). However, many treatment plans do not require movement of the patient during treatment. Provided the patient can be correctly positioned relative to the radiation source 22, that component may be deemed not necessary for those particular treatment plans.

If the faulty component is not needed for the particular treatment plan, the treatment can be allowed to proceed (step 206). Thus, the controller 38 may transmit one or more control signals to the system 10 to begin operation, or the controller may set a flag in the system 10 so that operation can proceed once a clinician indicates the patient is correctly positioned and ready for treatment.

If the faulty component is needed to deliver the treatment plan, the method proceeds to step 208, in which it is determined whether the function of the faulty component can be replicated or compensated for by other components of the system.

For example, one of either the first support mechanisms 18 (i.e. coarse motion) or the second support mechanisms 20 (i.e. fine motion) may develop a fault which results in that support mechanism being unable to adjust the bed 16 in a particular degree of freedom. In that case, the absent degree of freedom in the faulty support mechanism may be replaced by corresponding motion of the non-faulty support mechanism. For example, faults in one or more of the hexapod members may result in the hexapod being unable to move the bed in a particular direction. The movement in that direction may be replicated by corresponding movement of the primary support mechanism.

If the function of the faulty component can be easily replicated or compensated for by other components of the system, the treatment plan can be adapted in step 210 so that the function of the faulty component is replaced by other components. The treatment is allowed to proceed in step 206 once suitably adapted.

If the function of the faulty component cannot be replicated, the method proceeds to step 212 where the fault may be returned to the treatment planning apparatus. As explained above, the treatment planning apparatus formulates the treatment plan on the basis of a planning image of the patient (i.e. an image incorporating the target for treatment as well as the surrounding tissue and anatomical structures), a number of clinical objectives set by a clinician (e.g. a minimum dose for the target, a maximum dose for radiation-sensitive nearby structures, etc), and the constraints of the radiotherapy system which is to apply the therapy. The latter parameters can be adapted to include the fact that one of the components of the radiotherapy system is faulty. The treatment planning apparatus then proceeds to formulate a new, revised treatment plan, using the new information that one of the components of the radiotherapy system is faulty. The revised treatment plan should therefore be formulated such that the faulty component is not used. The treatment planning apparatus may use the same planning image as before, and the same clinical objectives. The method then moves back to step 200, in which the revised treatment plan is received.

Of course, some components are essential to any treatment plan, and thus a fault in any one of them makes the radiotherapy apparatus effectively inoperable. For example, a fault in the linear accelerator may make the generation of ionizing radiation impossible and in that case no treatment can be carried out until the system is repaired. However, the facility in which the system is installed (e.g. a hospital) may have more than one radiotherapy system with the same or different capabilities. In that case, the treatment may be carried out on one of the other radiotherapy systems installed at the facility. The method therefore proceeds to step 214, where it is determined whether there are any other radiotherapy systems at the facility or other nearby facilities which have the necessary components and/or configuration to implement the treatment plan. This is more likely if the systems have been configured to the same specifications, as described in U.S. patent application Ser. No. 13/054,732 (publication no US 2011-0121763), assigned to the Assignee of this application. If there are, the patient can be scheduled to have the treatment on that system (step 216), using the treatment plan received in step 200. Systems at the same facility may be chosen in preference to systems at other facilities. If there are no other suitable systems available, then the options for continuing therapy have been exhausted and the patient cannot be treated at any nearby facility using the available systems. The method therefore ends in step 218.

The method may be implemented by the controller 38, and may be embodied in a computer program for execution by one or more processors.

Embodiments of the present invention therefore provide a method and a computer program product for managing radiotherapy in a medical facility. In the event that a component of a radiotherapy system develops a fault, embodiments of the present invention provide that proposed treatment plans are evaluated to see whether the faulty component is needed for their delivery. If the component is not needed, the treatment is allowed to proceed. If the component is needed, various further steps are proposed which may allow the treatment to go ahead. This is expected to lead to greater availability of radiotherapy systems to treat patients, with consequent improvements in treatment times.

Those skilled in the art will appreciate that various amendments and alterations can be made to the embodiments described above without departing from the scope of the invention as defined in the claims appended hereto.

The invention claimed is:

1. A method of operating a radiotherapy system, comprising:
receiving a treatment plan to be carried out using the radiotherapy system;
detecting a fault in a component of the radiotherapy system;

determining whether the component is needed for delivery of the treatment plan; and if the component is not needed for delivery of the treatment plan, allowing the radiotherapy system to execute the treatment plan.

2. The method according to claim 1, further comprising:

if the component is needed for delivery of the treatment plan, preventing the radiotherapy system from executing the treatment plan.

3. The method according to claim 1, further comprising:

if the component is needed for delivery of the treatment plan, informing a treatment planning apparatus that the component has a fault; and receiving a revised treatment plan in which the component is not used.

4. The method according to claim 1, further comprising:

determining whether a function carried out by the component can be replicated by one or more further components of the radiotherapy system; and if the function can be replicated by one or more further components, adapting the treatment plan such that the function is replicated by the one or more further components.

5. The method according to claim 1, further comprising:

if the component is needed for delivery of the treatment plan, determining whether a second radiotherapy system is available which can deliver the treatment plan; and if a second radiotherapy system which can deliver the treatment plan is available, scheduling the treatment plan for delivery on the second radiotherapy system.

6. The method according to claim 1, wherein the component comprises a leaf of a multi-leaf collimator.

7. The method according to claim 6, wherein the step of determining whether the component is needed for delivery of the treatment plan includes determining whether the treatment plan includes instructions for the movement of the leaf of the multi-leaf collimator.

8. The method according to claim 6, wherein the step of detecting a fault comprises detecting that actuation of the leaf is impaired, or detecting that a marker on the leaf is not visible.

9. The method according to claim 1, wherein the component comprises a patient support which can be adjusted in one or more degrees of freedom, and wherein the step of detecting a fault comprises detecting that movement of the patient support is impaired in one of said one or more degrees of freedom.

10. The method according to claim 9, wherein the step of determining whether the component is needed for delivery of the treatment plan includes determining whether the treatment plan includes instructions for movement of the patient support along the degree of freedom.

11. The method according to claim 9, further comprising determining whether movement of the patient support along the degree of freedom can be replicated by corresponding movement of one or more further components of the radiotherapy system.

12. The method according to claim 1, wherein the component comprises an imaging apparatus, and the step of determining whether the component is needed for delivery of the treatment plan includes determining whether the treatment plan includes instructions for imaging the patient.

13. The method according to claim 1, wherein the component is for at least one of shaping a radiation beam and directing the radiation beam relative to a patient.

14. A non-transitory computer-readable medium comprising code which, when executed by a computer, causes the computer to carry out the method according to claim 1.

* * * * *